United States Patent [19]

Dennis et al.

[11] 3,987,065

[45] Oct. 19, 1976

[54] PURIFICATION OF ALKYLENE OXIDES

[75] Inventors: Kent S. Dennis; Edwin C. Steiner, both of Midland, Mich.

[73] Assignee: The Dow Chemical Company, Midland, Mich.

[22] Filed: Dec. 13, 1972

[21] Appl. No.: 314,792

[52] U.S. Cl. .......... 260/348 R
[51] Int. Cl.² .......... C07D 301/32
[58] Field of Search .......... 260/348 R

*Primary Examiner*—Norma S. Milestone
*Attorney, Agent, or Firm*—Stephen Hoynak; Glwynn R. Baker

[57] ABSTRACT

Monomeric epoxides are purified by mixing with a hydrocarbyl alkali metal. The requisite amount of hydrocarbyl lithium is readily detectable by a change in color of a suitable indicator. The monomeric epoxide so purified can be rapidly and completely polymerized to yield high molecular weight homopolymers or copolymers.

18 Claims, No Drawings

PURIFICATION OF ALKYLENE OXIDES

BACKGROUND OF THE INVENTION

Monomeric epoxides contain small quantities of impurities containing active hydrogen which must be removed to prepare polymers with molecular weights above 20,000. The impurities when present even in a few ppm range slow the polymerization rate by a factor of 10 or more.

The usual impurities include glycols, alcohols and traces of water. Prior art procedures for purifying epoxides have included the addition of calcined KOH or $CaH_2$ and then distilling. However, KOH and CaO are known polymerization initiators, so that during distillation, explosive polymerizations can take place. Even under the most careful operating conditions, when using prior art procedures, removal of all impurities is difficult. Failure to remove these impurities makes it very difficult to make polymers having a molecular weight above 20,000 with any degree of consistency.

It is apparent, therefore, that a method by which impurities can be removed or made innocuous is highly desirable.

We have found a simple, yet very effective, method for purifying monomeric epoxides, to provide monomers which homo- or copolymerize rapidly, substantially completely, and produce high molecular weight polymers consistently. The epoxides are particularly useful for forming block copolymers of the structure ERE where R is a hydrocarbon chain and each E represents a polyether group derived from an epoxide.

SUMMARY OF THE INVENTION

This invention relates to a method of purifying monomeric epoxides by adding a hydrocarbyl lithium compound or a mixture thereof to an impure epoxide in an amount sufficient to react with substantially all the impurities which react with the lithium compound, desirably in the presence of a color changing indicator, and desirably separating the epoxide from the mixture.

Included among the vicinal epoxides are ethylene oxide, 1,2-propylene oxide, 1,2-butylene oxide, 2,3-butylene oxide, 1,2-pentylene oxide, 2,3-pentylene oxide or any other oxirane-type epoxide having from 2 to about 8 C atoms.

The hydrocarbyl lithium compound can be any compound having a lithium metal attached directly to a carbon atom of a hydrocarbon group. The hydrocarbyl group attached to the lithium can be any alkyl or aryl group but the alkyl groups are preferred, particularly those having 1 to about 6 C atoms. Aryl hydrocarbon groups preferably contain 1 to about 3 rings, which preferably are 6-membered. Included among the latter are phenyl, naphthyl and anthracyl groups. Mixtures of any two or more of the above lithium hydrocarbyl compounds can be used.

Although an indicator is not absolutely essential, it is preferred to use a compound which changes color when the requisite amount of hydrocarbyl lithium compound is added for complete reaction with the active hydrogen of the impurities. In this manner, only minute amounts of excess hydrocarbyl alkali metal are added. Representative indicators are 9-aryl fluorenes or 9-alkyl fluorenes. However, any other indicator which changes color after the hydrocarbyl lithium has reacted with impurities is satisfactory. The color of the mixture changes to yellow with 9-phenyl fluorene as the indicator, and to red when 9-methyl fluorene is used as the indicator It is apparent that an alternative procedure for carrying out the process is to titrate a sample of known weight or volume and thereafter calculate the amount of lithium hydrocarbyl needed for a particular batch of epoxide and adding such amount thereto.

The purification step is preferably carried out in liquid phase, and preferably at temperatures not appreciably higher than about 0° C. When ethylene oxide is the epoxide, it is preferably cooled to about −50° C. during the titration with the hydrocarbyl lithium.

Pressure other than that required to maintain the epoxide liquid is not needed, as it has no effect on the purification reaction.

After purification, the epoxide can be separated, if desired, preferably by distillation, with or without vacuum, although any other procedure such as centrifuging or crystallization can also be employed. With Li hydrocarbyls, it is not necessary to purify the epoxide prior to polymerization for the reason that the lithium derivatives LiOH, LiOR, etc., are not polymerization catalysts for the epoxides under the purification conditions.

The examples which follow are intended to exemplify, but not to limit the invention. All parts are given by weight unless specifically indicated otherwise.

EXAMPLE 1

This example is intended to show that a purified ethylene oxide will readily form a block copolymer with a "living" styrene, α-methylstyrene copolymer.

All glassware was baked in an oven at about 100° C. before using. All flasks were evacuated and flushed with nitrogen before addition of any ingredient and all operations were carried out under nitrogen or under vacuum.

Tetrahydrofuran (THF) was purified by distilling it from a Na/naphthalene complex.

A "living" block copolymer of styrene and α-methylstyrene was prepared by adding 322.9 g. of THF, 28.0 g. of α-methylstyrene, which was dried over $CaH_2$, and 4.9 g. of K to a three-necked one-liter polymerization flask equipped with a stirrer and two dry ice condensers. The mixture was stirred overnight at autogenous temperature. On titration, it was shown to contain 0.3059 meq. of organopotassium per g.

At this stage, 75.1 g. of styrene, which was also dried overnight with $CaH_2$, was distilled under vacuum and mixed with 86.3 g. of THF. This solution was added dropwise to the flask at 0° C.

Ethylene oxide was condensed from a cylinder into a flask cooled in liquid nitrogen. Then a dry ice bath was substituted for the liquid nitrogen. A few crystals of 9-phenylfluorene dissolved in about 1 ml. THF were added. The liquid was then titrated with 0.5 N n-BuLi to a yellow end point. This required about 1.5 ml. The flask containing the titrated ethylene oxide was attached to the polymerization flask containing the "living" copolymer of styrene-α-methyl styrene, and 95.9 g. of ethylene oxide was distilled. As the ethylene oxide distilled into the reaction mixture at 0° C., the color changed from dark red to pale orange. When the ice bath was removed, the solution began to warm, so the bath was replaced. This happened a second time, after which the solution remained at about room temperature. After standing overnight, 6.34 g. of acetic acid was added to terminate the reaction. The contents of the flask weighed 601 g. The material added to the flask weighed 609 g., so there was a loss of about 8 g. ethylene oxide to the atmosphere.

The solution was centrifuged to remove potassium acetate and then devolatilized at about 115° C. to give 188 g. polymer out of an expected 199 g. This eleven-gram loss compared closely with the eight-gram loss of EO. The IR spectrum of the polymer showed a large ether band at about 9 $\mu$. The polymer was a stiff, gummy material which dispersed completely in hot water.

EXAMPLE II

The procedures were much the same as Example I. The initiator, K/$\alpha$-methylstyrene, was prepared in a separate flask by mixing:

140 ml. tetrahydrofuran
11.7 ml. $\alpha$-methylstyrene
2.0 g. K and stirring overnight. Titration showed the solution to be 0.287 N in organopotassium. To the polymerization flask, described in Example I, was added:

393.29 g. tetrahydrofuran
1.3 ml. complex to blank the THF
26.71 g. complex solution to polymerize the ethylene oxide. Ethylene oxide was purified as in Example I, and 98.97 g. was distilled into the polymerization flask. At first, the material in the flask turned cloudy, then it agglomerated, but as more ethylene oxide was added, the solution became clear. The flask was warmed periodically to about 40° C., but it always cooled back to room temperature. After all the ethylene oxide was added, the mixture remained warm for 2 to 3 hours. It was allowed to stir overnight. The color was light orange. The next morning, the solution was still orange, and an additional 88.90 g. ethylene oxide was distilled into it. The same warming behavior resulted, and again it was allowed to stir overnight. The following morning the solution was gelled with precipitate, but this dissolved on slight warming to about 30° C. About 1.0 ml. acetic acid was added to terminate the reaction. The contents of the flask weighed 603 g. — expected weight was 610 g. The solution was devolatilized at 120° C. under vacuum and gave 184 g. polymer out of an expected 191 g., which agreed well with the loss of ethylene oxide to the atmosphere. The polymer was waxy, and soluble in water.

EXAMPLE III

A K/$\alpha$-methylstyrene complex was prepared by adding 1.26 g. K metal to 8.5 ml. $\alpha$-methylstyrene (stored over $CaH_2$) dissolved in 258.4 g. of pre-dried THF.

45.1 g. of ethylene oxide was condensed in a receiver which was cooled with liquid nitrogen. A few crystals of 9-phenylfluorene dissolved in 1 ml. of THF were added and then the ethylene oxide was titrated with 0.55 ml. of 0.5N n-BuLi to a yellow end point. The active hydrogen-containing impurity, calculated as water, was 110 ppm.

The so-titrated solution was added all at once into the flask containing the K $\alpha$-methylstyrene initiator. The initiator precipitated immediately, but after about 2 hours, it dissolved to form an orange-colored solution. After 4 hours, the mixture was very viscous and warm. The mixture was stirred overnight. The mixture contained 14.5% solids.

We claim:

1. A method of purifying a monomeric vicinal epoxide having from 2 to about 8 C atoms or mixtures thereof, contaminated with compounds having active hydrogen, comprising adding at least one lithium hydrocarbyl compound to said epoxide at a temperature between about 0 and about −50° C., the amount of said lithium hydrocarbyl compound being sufficient to react with substantially all the impurities which react with the said lithium hydrocarbyl compound, the hydrocarbyl group being an alkyl group of from 1 to about 6 C atoms or an aromatic group having from 1 to 3 rings each having 6 members.

2. The method of claim 1 in which the epoxide is ethylene oxide and the temperature is about −50° C.

3. The method of claim 1 in which a color changing indicator is employed.

4. The method of claim 3 in which the indicator is a 9-aryl or 9-alkyl fluorene.

5. The method of claim 4 in which the indicator is 9-phenyl fluorene.

6. The method of claim 4 in which the indicator is 9-methyl fluorene.

7. The method of claim 1 in which the epoxide is separated from the mixture after purification.

8. The method of claim 1 in which the epoxide is styrene oxide.

9. The method of claim 1 in which the epoxide is 1,2-propylene oxide.

10. The method of claim 1 in which the epoxide is 1,2-butylene oxide.

11. The method of claim 1 in which the hydrocarbon group of the lithium hydrocarbyl compound is an alkyl group of 1 to 6 carbon atoms.

12. The method of claim 11 in which the hydrocarbon group is an n-butyl group.

13. The method of claim 1 in which the hydrocarbon group of the lithium hydrocarbyl compound is an aryl group of from 1 to 3 six membered rings.

14. The method of claim 13 in which the aryl group is phenyl.

15. The method of claim 13 in which the aryl group is naphthyl.

16. The method of claim 13 in which the aryl group is anthracyl.

17. The method of claim 1 in which the epoxide is in liquid state during the addition of the lithium hydrocarbyl compound.

18. The method of claim 17 in which the epoxide is ethylene oxide.

* * * * *